(12) United States Patent
Tsukamoto

(10) Patent No.: US 10,471,221 B2
(45) Date of Patent: Nov. 12, 2019

(54) NEEDLE ATTACHMENT AND DETACHMENT ASSIST DEVICE

(71) Applicant: NHK SPRING CO., LTD., Yokohama-shi, Kanagawa (JP)

(72) Inventor: Yasumasa Tsukamoto, Aiko-gun (JP)

(73) Assignee: NHK SPRING CO., LTD., Tokyo (JP)

( * ) Notice: Subject to any disclaimer, the term of this patent is extended or adjusted under 35 U.S.C. 154(b) by 230 days.

(21) Appl. No.: 15/460,905

(22) Filed: Mar. 16, 2017

(65) Prior Publication Data
US 2017/0266393 A1  Sep. 21, 2017

(30) Foreign Application Priority Data
Mar. 17, 2016  (JP) .................................. 2016-053873

(51) Int. Cl.
*A61M 5/32* (2006.01)
*A61M 5/34* (2006.01)

(52) U.S. Cl.
CPC .......... *A61M 5/3276* (2013.01); *A61M 5/343* (2013.01); *A61M 5/347* (2013.01); *A61M 2209/084* (2013.01)

(58) Field of Classification Search
CPC .. A61M 5/3205; A61M 5/3276; A61M 5/343; A61M 5/347; A61M 5/348; A61M 2005/3206; A61M 2209/084; B25B 11/02; Y10T 29/53657; Y10T 29/5367; Y10T 29/53683
See application file for complete search history.

(56) References Cited

U.S. PATENT DOCUMENTS 4,453,648 A * 6/1984 Harris ....................... B65F 1/16
                                                                    206/370
4,576,281 A * 3/1986 Kirksey .............. A61M 5/3205
                                                                    206/366
(Continued)

FOREIGN PATENT DOCUMENTS

CN        102470074 A    5/2012
JP         3039408 U     7/1997
(Continued)

OTHER PUBLICATIONS

Japanese Office Action dated May 28, 2019 (and English translation thereof) issued in counterpart Japanese Application No. 2016-053873.

(Continued)

*Primary Examiner* — Tyrone V Hall, Jr.
(74) *Attorney, Agent, or Firm* — Holtz, Holtz & Volek PC

(57) ABSTRACT

A needle attachment and detachment assist device includes a frame body, a syringe guide jig, and a needle guide jig. A guide hole is formed in the syringe guide jig. In the needle guide jig, a needle insertion hole is formed on a central axis of the guide hole. The needle insertion hole includes a center hole portion and a rib guide groove. When a syringe is inserted into the guide hole, and a needle member is further inserted into the needle insertion hole, rotation prevention of the needle member is achieved. In this state, when the syringe is rotated in a first direction, the needle member can be clamped to a thread portion of the syringe. When the syringe is rotated in a second direction, the needle member can be loosened.

6 Claims, 7 Drawing Sheets

(56) References Cited

U.S. PATENT DOCUMENTS

| | | | | |
|---|---|---|---|---|
| 4,989,307 A | * | 2/1991 | Sharpe | A61M 5/3205 |
| | | | | 128/917 |
| 5,933,936 A | * | 8/1999 | Wand | A61M 5/3205 |
| | | | | 29/239 |
| 6,439,276 B1 | * | 8/2002 | Wood | A61M 5/1782 |
| | | | | 141/27 |
| 6,909,251 B2 | * | 6/2005 | Cooley | A61M 5/3205 |
| | | | | 318/139 |
| 8,900,212 B2 | | 12/2014 | Kubo | |
| 2012/0310171 A1 | | 12/2012 | Liversidge | |

FOREIGN PATENT DOCUMENTS

| | | |
|---|---|---|
| JP | 2002085560 A | 3/2002 |
| JP | 2013517920 A | 5/2013 |
| JP | 2014018456 A | 2/2014 |

OTHER PUBLICATIONS

Chinese Office Action dated Aug. 22, 2019 (and English translation thereof) issued in counterpart Chinese Application No. 201710148008.6.

\* cited by examiner

NEEDLE ATTACHMENT AND DETACHMENT ASSIST DEVICE

CROSS-REFERENCE TO RELATED APPLICATIONS

This application is based upon and claims the benefit of priority from prior Japanese Patent Application No. 2016-053873, filed Mar. 17, 2016, the entire contents of which are incorporated herein by reference.

BACKGROUND OF THE INVENTION

1. Field of the Invention

The present invention relates to a needle attachment and detachment assist device for use in attaching a needle member of a syringe unit used for a dispenser to a syringe or detaching the same from the syringe.

2. Description of the Related Art

FIG. 1 shows an example of an application device which applies a conductive resin A to a workpiece W. An example of the workpiece W is a head gimbal assembly used in a hard disk drive. In the case of the workpiece W, for the mounting of an actuator element B, the conductive resin. A such as silver paste having relatively high viscosity is used. The conductive resin A is one example of a liquefied or paste-like fluid.

The application device 1 comprises a movable stage 2, a drive mechanism 3, a lifting stage 4, a lift mechanism 5, a stage controller 6, a dispenser 7, and the like. The movable stage 2 can hold a plurality workpieces W arranged at a predetermined pitch. The drive mechanism 3 moves the movable stage 2 in the direction indicated by arrow M1. The lifting stage 4 is vertically movable. The lift mechanism 5 moves the lifting stage 4 in the direction indicated by arrow M2. The dispenser 7 ejects the conductive resin A toward an application target portion in the workpiece W.

The dispenser 7 is constituted of a syringe unit 10, a metering section 11, an air supply source 12, a control unit 13, and the like. The metering section 11 supplies a specified amount of conductive resin A to the syringe unit 10. The syringe unit 10 includes a syringe 15, and a needle member 16 attached to a lower end of the syringe 15. The conductive resin A supplied to the syringe 15 is discharged from a distal end of the needle member 16 toward the workpiece W.

The needle member 16 includes a luer-lock-type removable joint 18. The needle member 16 is fixed to the syringe 15 via the joint 18. The luer-lock-type joint 18 includes a thread portion formed at an end portion of the syringe 15, and a convex portion formed on the needle member 16. As the convex portion is screwed into the thread portion of the syringe 15, the needle member 16 is fixed to the syringe 15. An example of the luer-lock-type joint is disclosed in JP 2002-85560 A (Patent Literature 1) or JP 2013-517920 A (Patent Literature 2).

The syringe 15 and the needle member 16 are coupled to each other via the luer-lock-type joint 18. When the high-viscosity conductive resin A, for example, is used, the conductive resin A is supplied to the syringe unit 10 at high pressure. Accordingly, if the joint 18 is loosened, the conductive resin A may leak outside from a gap in the joint 18, or the needle member 16 may detach from the syringe 15.

Hence, conventionally, when the needle member 16 is to be attached to the syringe 15, an operation of achieving tight clamping at the joint 18 has been carried out. For example, the needle member 16 is grasped by a tool such as tweezers or pliers, and the syringe 15 is rotated by hand. However, since the needle member 16 is a small component, it is not easy to handle it manually. Further, such a conventional method leaves room for improvement in that the needle member 16 may be deformed by an inadvertent contact with the surrounding object, or an operator may be hurt by a tip of the needle member 16.

BRIEF SUMMARY OF THE INVENTION

An object of the present invention is to provide a needle attachment and detachment assist device capable of safely and securely performing the operation of attaching a needle member of a syringe unit to a syringe, and detaching the needle member from the syringe.

An embodiment relates to a needle attachment and detachment assist device for a syringe unit in which a syringe and a needle member are fixed to each other via a luer-lock-type joint. The needle member includes a body and a rib extending in a direction along an axis of the body. The needle attachment and detachment assist device includes a frame body, a syringe guide jig provided on an upper part of the frame body, and including a guide hole through which the syringe is inserted, and a needle guide jig provided on a lower part of the syringe guide jig to be opposed to the syringe guide jig. The needle guide jig includes a needle insertion hole, and the needle insertion hole includes a center hole portion located on a central axis of the guide hole, and a rib guide groove into which the rib is inserted.

According to the needle attachment and detachment assist device structured as described above, while guiding the syringe by the syringe guide jig, the needle member can be inserted into the needle guide jig. Further, as the needle member is held by the needle guide jig, the needle member can be prevented from rotating. When the syringe is rotated in this state, it is possible to fasten the needle member to a thread portion of the syringe, or loosen the same from the thread portion of the syringe. Accordingly, it is possible to prevent a tip of a needle of the needle member from contacting an operator or prevent the needle from contacting the surrounding object, and to safely and securely perform the operation of attaching or detaching the needle member.

The frame body may include a pair of side plates, and a needle chamber which is defined by the needle guide jig and the pair of side plates on a lower surface side of the needle guide jig. Further, the frame body may include a lower plate formed of an optically transparent material, and the lower plate may be arranged at a position facing the needle chamber. The needle attachment and detachment assist device may include, an opening chamber including an opening of a size which enables the needle member to be taken out therefrom, between the syringe guide jig and the needle guide jib. The guide hole of the syringe guide jig should preferably include an inner surface formed such that an internal diameter of the guide hole is reduced in a tapered way in cross section. Further, the body of the needle member may comprise a cylindrical proximal portion and the rib extending from the proximal portion in the direction along the axis of the body, and a recess portion where a front end of the proximal portion of the needle member contacts may be provided around the center hole portion located at an upper surface of the needle guide jig.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
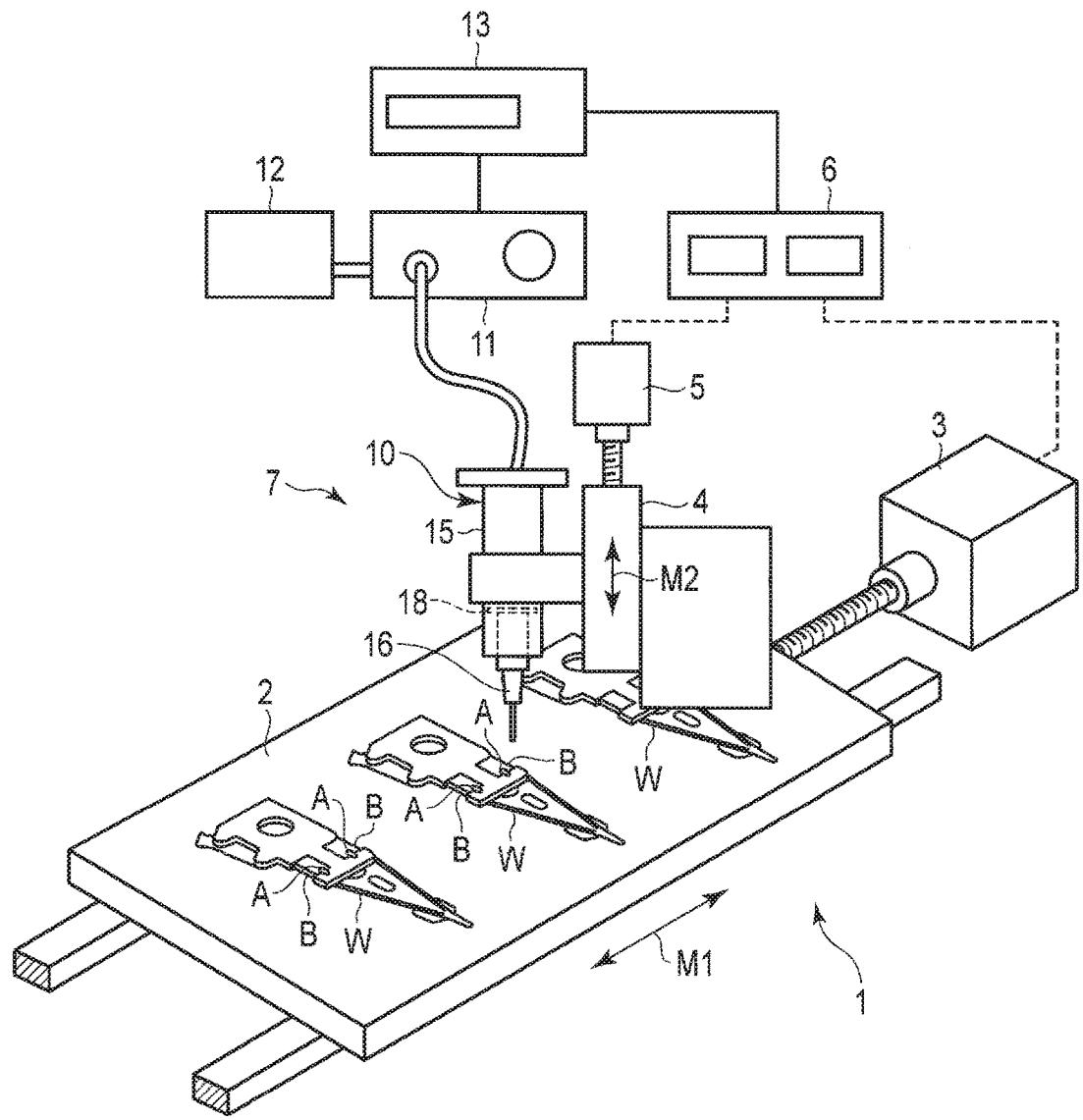
FIG. 1 is a perspective view schematically showing an example of an application device comprising a dispenser.
Figure 2:
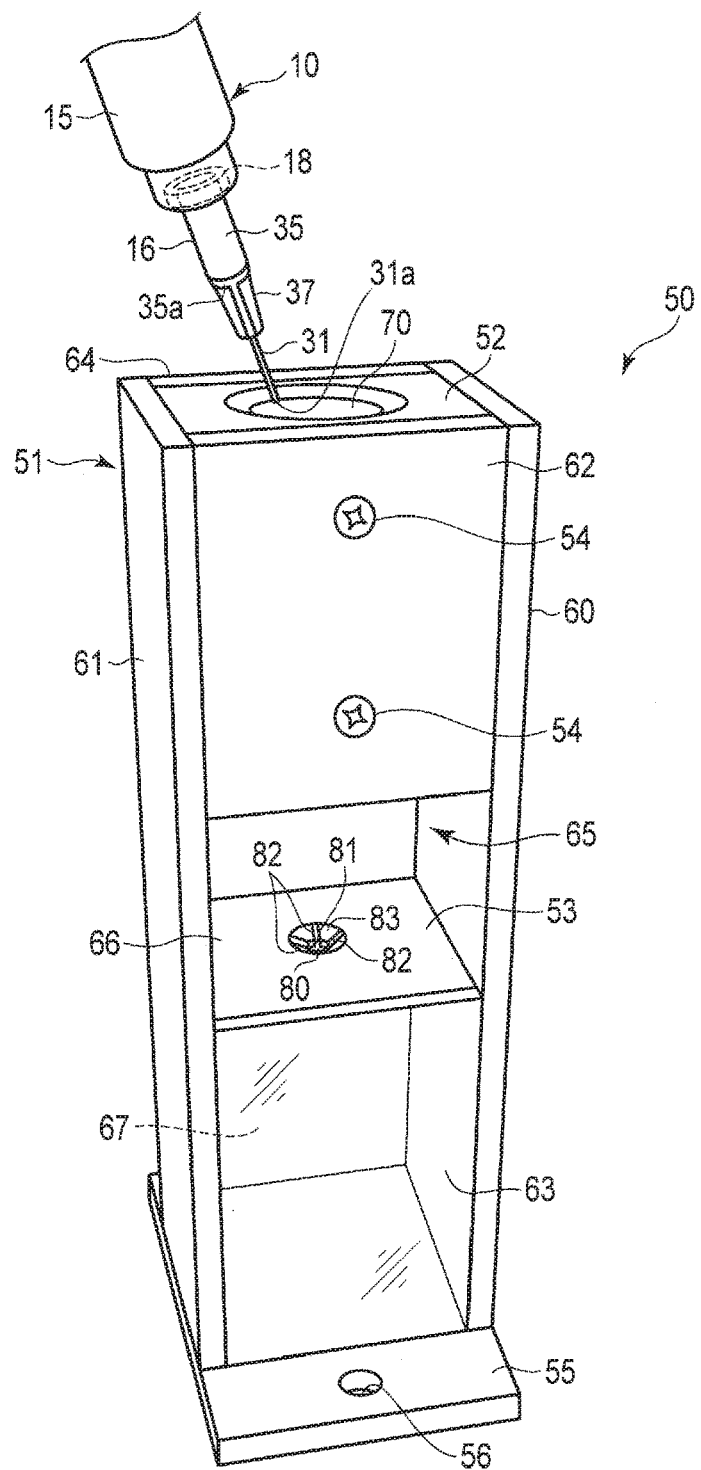
FIG. 2 is a perspective view showing a needle attachment and detachment assist device, and a part of a syringe unit according to one embodiment of the present invention.

FIG. 2 shows a part of a syringe unit 10, and a needle attachment and detachment assist device 50 according to an embodiment of the present invention. First, an example of the syringe unit 10 will be described.

Figure 3:
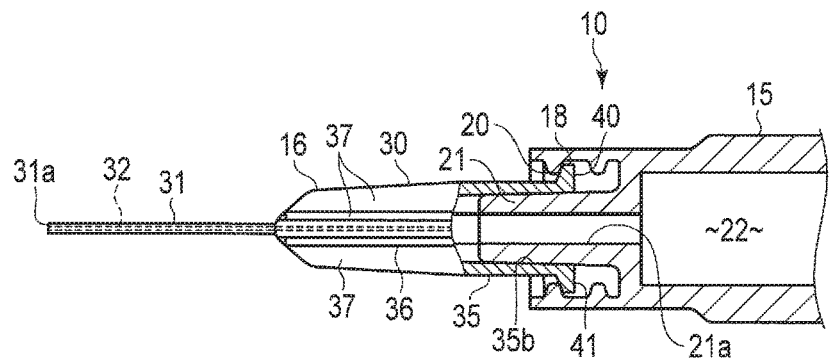
FIG. 3 is a side view showing a part of the syringe unit in cross section.

FIG. 3 shows the interior of the syringe unit 10. The syringe unit 10 includes a syringe 15 and a needle member 16. The needle member 16 is inserted and attached to a distal end portion of the syringe 15. At an end portion of the syringe 15, a thread portion (a female thread portion) 20 is formed. The thread portion 20 constitutes a part of a luer-lock-type joint 18. A cylindrical portion 21 is formed inside the thread portion 20. A flow passage portion 21a is formed inside the cylindrical portion 21. The flow passage portion 21a communicates with a fluid pressurizing chamber 22 inside the syringe 15.

Figure 4:
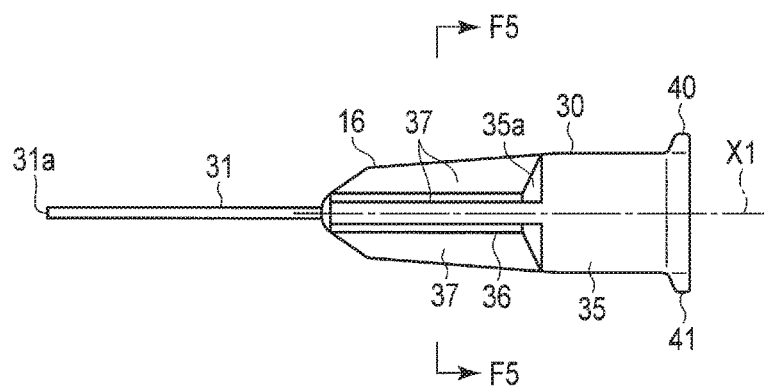
FIG. 4 is a side view of a needle member of the syringe unit shown in FIG. 3.
Figure 5:
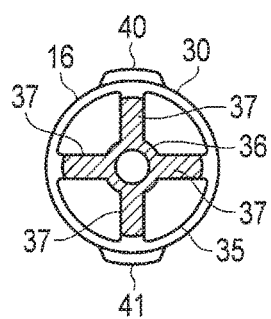
FIG. 5 is a cross-sectional view of the needle member taken along line F5-F5 of FIG. 4.

FIG. 4 is a side view of the needle member 16, and FIG. 5 is a cross-sectional view of the needle member 16 in a radial direction thereof taken along line F5-F5 of FIG. 4. The needle member 16 includes a body 30 made of resin, and a needle 31 made of metal attached to the body 30. A flow hole 32 (FIG. 3) is formed inside the needle 31. The needle 31 extends in a direction along axis X1 (FIG. 4) of the body 30.

The body 30 made of resin includes a proximal portion 35 in a substantially cylindrical (tubular) shape, a tube portion 36, and four ribs 37 integrally. The tube portion 36 extends in the direction along axis X1 of the body 30 from a front end 35a of the proximal portion 35. The four ribs 37 are formed around the tube portion 36. As shown in FIG. 5, the ribs 37 are formed at regular intervals to be spaced apart from each other by 90° in a circumferential direction about the tube portion 36. Each of these ribs 37 extends in the direction along axis X1 of the body 30. Convex portions 40 and 41 are formed at a rear end of the body 30. The convex portions 40 and 41 constitute a part of the luer-lock-type joint 18. The convex portions 40 and 41 are shaped such that the convex portions 40 and 41 can be screwed into the thread portion 20 of the syringe 15.

In the proximal portion 35 of the needle member 16, an inner surface 35b (FIG. 3) is formed. The cylindrical portion 21 of the syringe 15 fits with this inner surface 35b in a fluid-tight manner. In a state in which the proximal portion 35 is fitted onto the cylindrical portion 21, the needle member 16 is rotated so that the convex portions 40 and 41 are screwed into the thread portion 20. Thereby, the proximal portion 35 of the needle member 16 fits with the cylindrical portion 21 in a fluid-tight manner. Thereby, the needle member 16 is fixed to the syringe 15, and the fluid pressurizing chamber 22 communicates with the flow hole 32 of the needle 31 through the flow passage portion 21a. That is, luer-lock coupling between the syringe 15 and the needle member 16 is achieved.

Next, the needle attachment and detachment assist device 50 will be described.

As shown in FIG. 2, the needle attachment and detachment assist device 50 comprises a box-shaped frame body 51, a block-like syringe guide jig 52, and a plate-like needle guide jig 53. The frame body 51 extends in a vertical direction. The syringe guide 52 is provided on the upper part of the frame body 51. The syringe guide jig 52 is fixed to the frame body 51 by a fixing member 54 such as a screw. The needle guide jig 53 is provided at a middle portion of the frame body 51 in the vertical direction. The needle guide jig 53 is arranged on a lower part of the syringe guide jig 52. The needle guide jig 53 is fixed to the frame body 51 in a state in which it is spaced apart from and opposed to a lower surface of the syringe guide jig 52. On a lower end of the frame body 51, a base portion 55 is provided. In the base portion 55, a through-hole 56 for fixing the frame body 51 to a workbench or the like, if needed, is formed.

The frame body 51 includes a pair of rectangular side plates 60 and 61, an upper plate 62, a lower plate 63, and a back plate 64. The upper plate 62 is secured to the upper part of each of the side plates 60 and 61 by adhesive bonding or the like on a front side of the frame body 51. The lower plate 63 is secured to the lower part of each of the side plates 60 and 61 by adhesive bonding or the like on the front side of the frame body 51. The back plate 64 is secured to the side plates 60 and 61 by adhesive bonding or the like on a back side of the frame body 51. At least the lower plate 63 of these plates 60, 61, 62, 63, and 64 is formed of an optically transparent material, for example, a transparent acrylic board.

An opening chamber 66 having an opening 65 is formed between the upper plate 62 and the lower plate 63. The opening chamber 66 is formed between the syringe guide jig 52 and the needle guide jig 53. The opening chamber 66 has a space sufficient for accommodating the needle member 16. The opening 65 is of a size which enables the needle member 16 on the needle guide jig 53 to be taken out.

On the lower surface side of the needle guide jig 53, a needle chamber 67 is formed. The needle chamber 67 is defined by the needle guide jig 53, the side plates 60 and 61, and the lower plate 63. The lower plate 63 formed of an optically transparent material is arranged at a position facing the needle chamber 67. Accordingly, the inside of the needle chamber 67 can be seen through.

Figure 6:
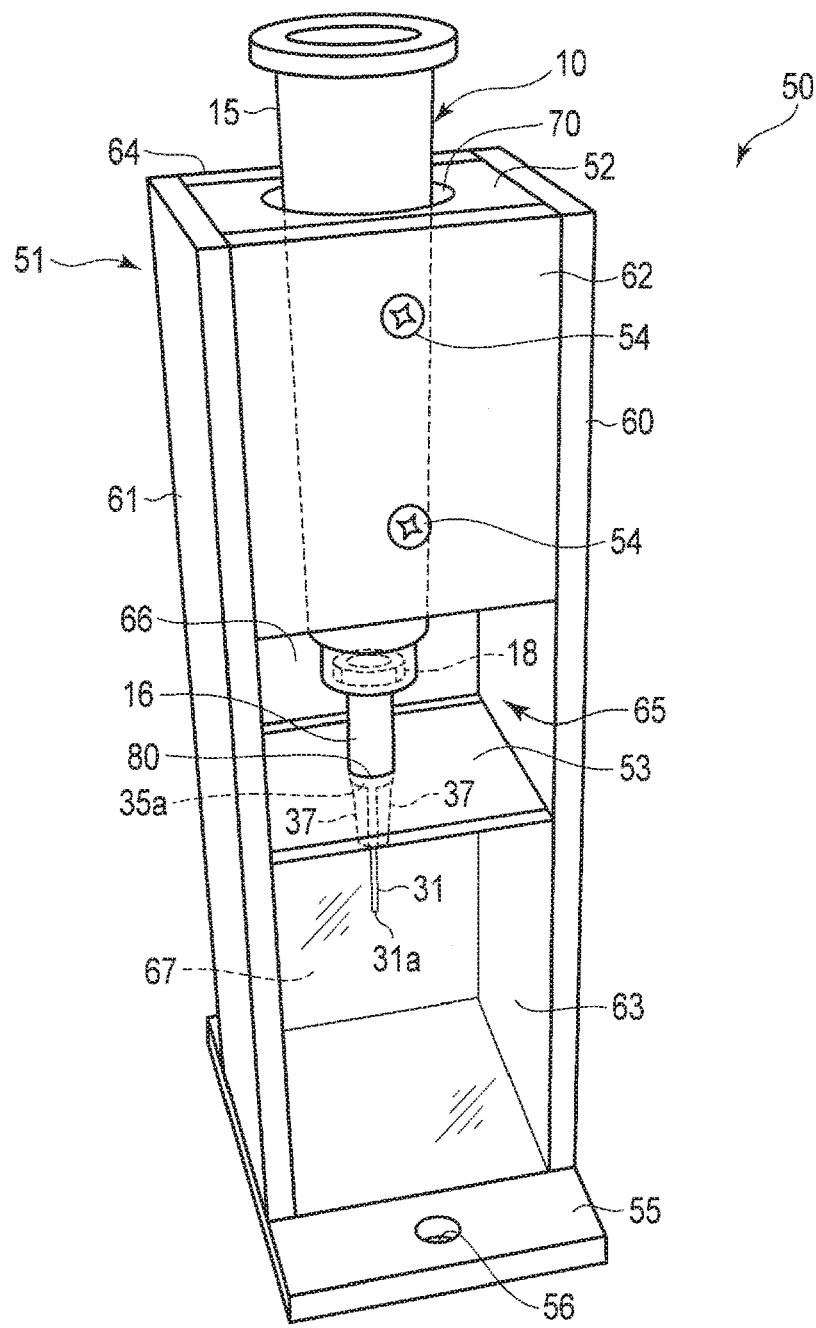
FIG. 6 is a perspective view showing the state in which the syringe unit is inserted into the needle attachment and detachment assist device shown in FIG. 2.
Figure 7:
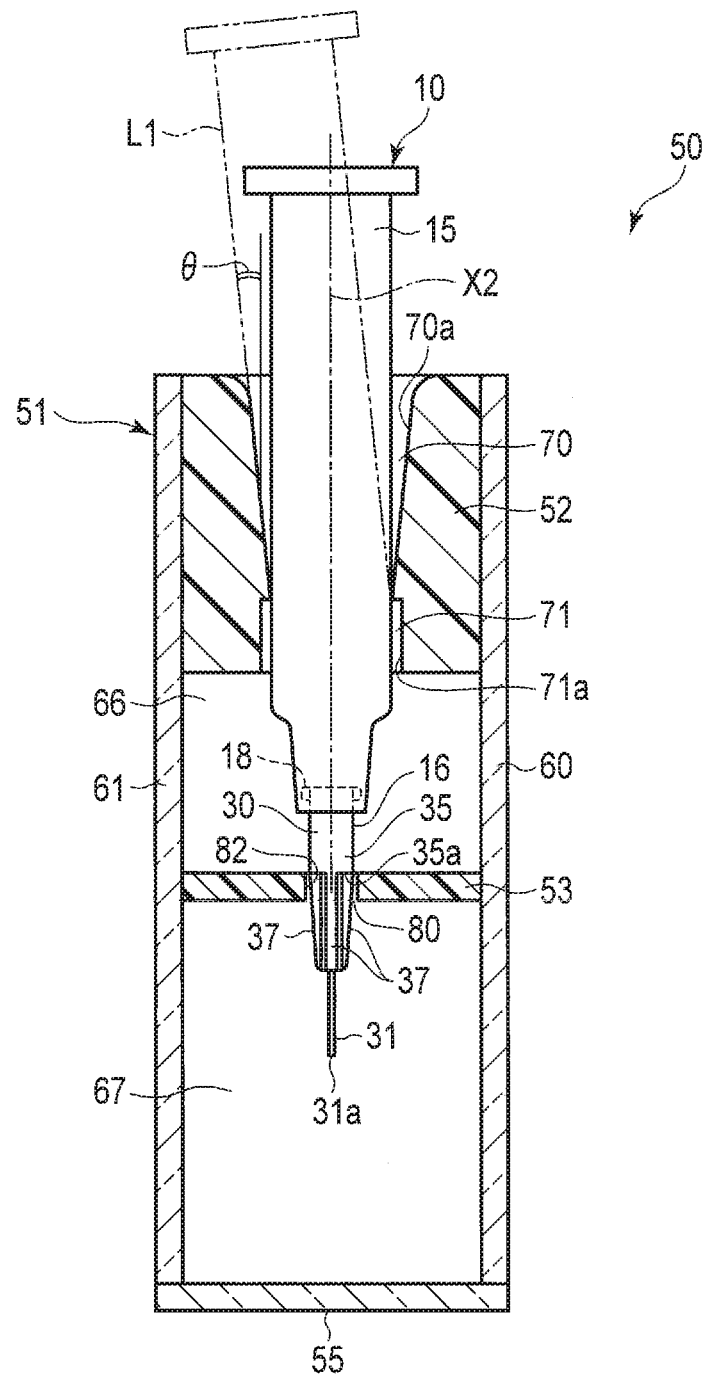
FIG. 7 is a longitudinal sectional view of the needle attachment and detachment assist device.

FIG. 6 shows the state in which the syringe unit 10 is inserted into the needle attachment and detachment assist device 50. FIG. 7 is a longitudinal sectional view of the needle attachment and detachment assist device 50 into which the syringe unit 10 is inserted. The syringe guide jig 52 includes a guide hole 70 and a communication port 71 which penetrate the syringe guide jig 52 in the vertical direction. The communication port 71 extends downward from a lower end of the guide hole 70. The guide hole 70 has an internal diameter which allows the syringe 15 to be inserted therein. Moreover, the guide hole 70 has a shape which constitutes a part of a cone, more specifically, is formed such that the internal diameter of the guide hole 70 is reduced downward in a tapered way in cross section.

The syringe guide jig 52 is formed of a material harder than the syringe 15. Moreover, the syringe guide jig 52 is formed of a low friction material to allow the syringe 15 to be slid smoothly relative to the guide hole 70 when the syringe 15 is inserted into the guide hole 70. The low friction material is, for example, polyamide resin. In contrast, the syringe 15 is made of a resin (for example, polypropylene) softer than the syringe guide jig 52. As shown by a two-dot chain line L1 in FIG. 7, the syringe 15 may be inserted obliquely. An inner surface 70a of the guide hole 70 is inclined at an angle θ which prevents a distal end 31a of the needle 31 from being in contact with an inner surface 70a of the guide hole 70 or an inner surface 71a of the communication port 71 during insertion of the syringe 15, when the syringe 15 is inserted into the guide hole 70 in an inclined manner.

Figure 8:
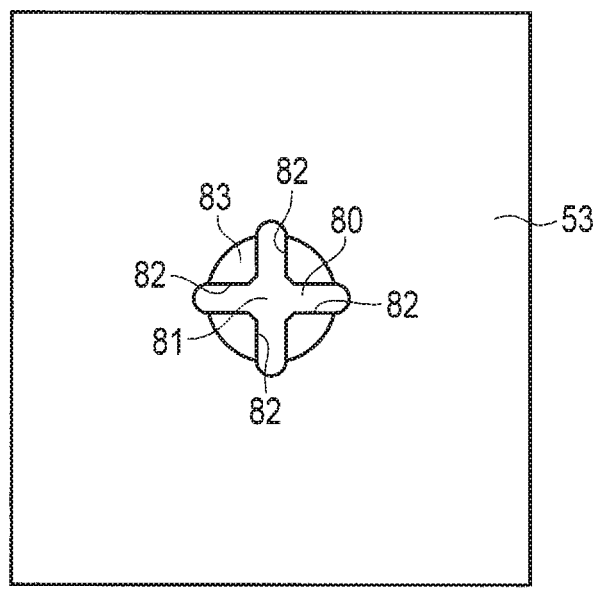
FIG. 8 is a plan view showing a needle guide jig of the needle attachment and detachment assist device.

FIG. 8 is a plan view of the needle guide jig 53. In the needle guide jig 53, a needle insertion hole 80 which penetrates the needle guide jig 53 in the vertical direction is formed. As shown in FIG. 8, the needle insertion hole 80 includes a center hole portion 81 formed in the center, and rib guide grooves 82 provided at four places. These rib guide grooves 82 are formed at regular intervals to be spaced apart from each other by 90° in a circumferential direction of the center hole portion 81. The center hole portion 81 is formed on central axis X2 (FIG. 7) of the guide hole 70. An internal diameter of the center hole portion 81 is slightly greater than an external diameter of the tube portion 36 of the needle member 16. Accordingly, the tube portion 36 can be inserted into the center hole portion 81.

Although the shape of the rib guide grooves 82 is not limited to the one illustrated in FIG. 8, one example of the rib guide grooves 82 shown in FIG. 8 is in a cross shape as seen from above the needle guide jig 53. That is, the rib guide grooves 82 are shaped in such a way the ribs 37 of the needle member 16 can be inserted in a direction along axis X1 of the body 30. On an upper surface of the needle guide jig 53, a recess portion 83 with the center hole portion 81 located at the center is formed. The recess portion 83 has a shape which constitutes a concave surface with an arc-shaped cross-section, for example, in accordance with the shape of the front end 35a of the proximal portion 35 of the needle member 16. When the needle member 16 is inserted into the needle insertion hole 80, the front end 35a of the proximal portion 35 of the needle member 16 comes into contact with the recess portion 83. In this state, the needle member 16 is prevented from rotating by the needle guide jig 53.

The needle guide jig 53 is made of a material harder than the body 30 of the needle member 16. Moreover, the needle guide jig 53 is formed of a low friction material to allow the needle member 16 to be slid smoothly relative to the needle insertion hole 80 when the needle member 16 is inserted into the needle insertion hole 80. The low friction material is, for example, polyamide resin. In contrast, the body 30 of the needle member 16 is made of a resin (for example, polypropylene) softer than the needle guide jig 53.

Next, steps of attaching the needle member 16 to the syringe 15 will be described.

An operator inserts the convex portions 40 and 41 of the needle member 16 into the thread portion 20 of the syringe 15 by hand. Further, by rotating the needle member 16 with relatively small force, the needle member 16 is tentatively attached to the thread portion 20 of the syringe 15.

As shown in FIG. 2, in a state in which the needle member 16 is attached to the syringe 15, the needle member 16 is directed downward. Further, the needle member 16 is inserted into the guide hole 70 from above the syringe guide jig 52. When the syringe unit 10 is inserted into the guide hole 70, while the syringe 15 is guided by the inner surface 70a of the guide hole 70, the distal end 31a of the needle 31 is directed toward the needle insertion hole 80.

The operator visually checks the needle 31 which is stuck out in the opening chamber 66 from the lower surface of the syringe guide jig 52 through the opening 65. Further, the needle member 16 is inserted into the needle insertion hole 80 with their positions adjusted so that the ribs 37 can be inserted into the rib guide grooves 82. As the ribs 37 are inserted into the rib guide grooves 82, an end point of rotation when the syringe 15 is rotated determined. The needle member 16 which has been inserted into the needle insertion hole 80 stops at a point where the front end 35a of the proximal portion 35 contacts the recess portion 83 of the needle guide jig 53. In this state, the needle member 16 is prevented from rotating by the needle guide jig 53.

When the needle member 16 reaches this state, the operator prevents the needle attachment and detachment assist device 50 from moving by holding it by hand, for example. Then, by firmly screwing the syringe 15 in a first direction (clockwise direction) by hand for clamping, the convex portions 40 and 41 are secured to the thread portion 20. In this way, retightening of the needle member 16 onto the syringe 15, that is, completion of clamping is achieved.

By an oversight on the operator's side, the operator may unintentionally attach a needle member of a different type (that is, a needle member of a different model number or size) to the syringe 15. However, in that case, the erroneous needle member cannot be inserted into the needle insertion hole 80 or the rib guide grooves 82, or abnormal play may be created between the needle member and the needle insertion hole 80. Consequently, the operator can recognize that the inserted needle member is of a type different from the type intended. Accordingly, an error that a needle member of a different type is set to the syringe 15 forcedly (incorrect assembly) can be prevented.

The above explanation applies to a case where the needle member 16 is fixed (clamped) to the thread portion 20 of the syringe 15 by using the needle attachment and detachment assist device 50. However, the needle attachment and detachment assist device 50 according to the present embodiment can also be used with the intent of removing (or loosening) the needle member 16 from the syringe 15. FIG. 6 shows the state in which the needle member 16 attached to the syringe 15 is inserted into the needle insertion hole 80 of the needle guide jig 53. When the syringe 15 in this state is rotated in a second direction (counterclockwise direction), fixing of the needle member 16 to the thread portion 20 can be loosened.

Figure 9:
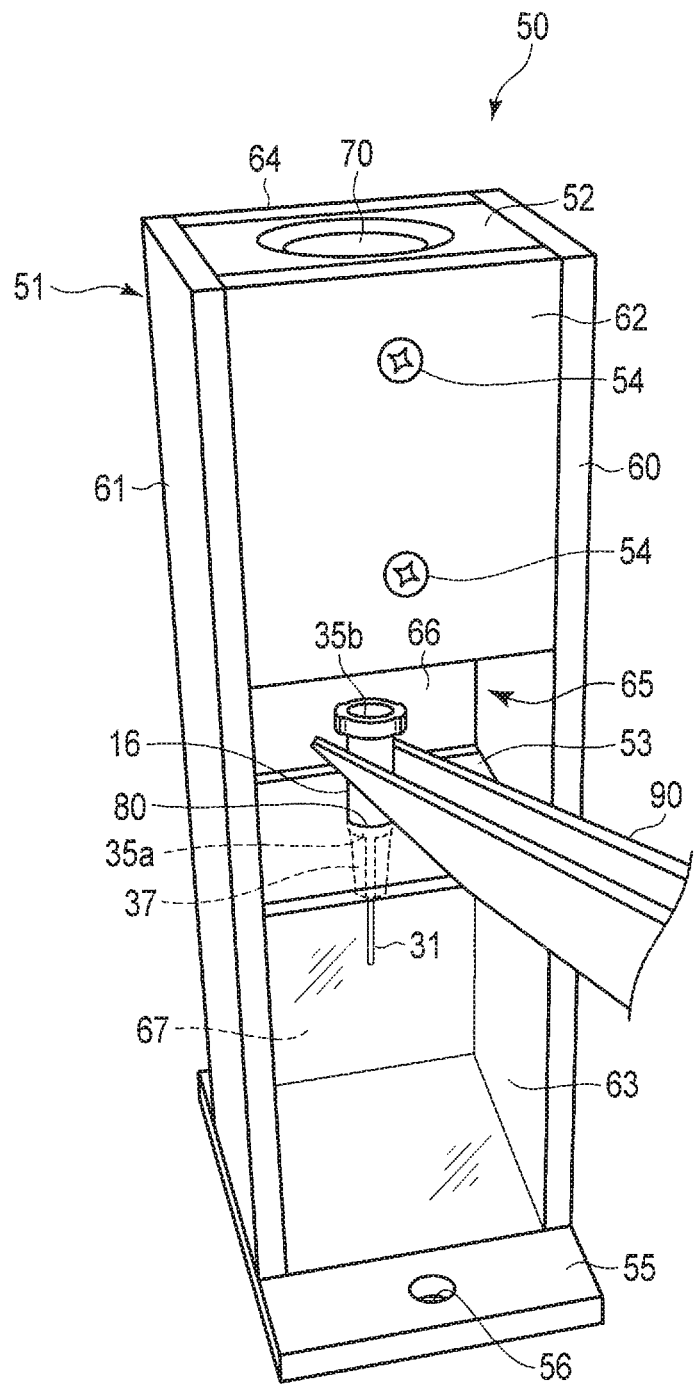
FIG. 9 is a perspective view sowing the state in which the needle member is left in the needle attachment and detachment assist device.

After loosening the needle member 16, the syringe unit 10 is taken out from the guide hole 70. In doing so, there may be a case where the needle member 16 is detached from the syringe 15 as shown in FIG. 9, and the needle member 16 is left on the needle guide jig 53. In that case, a tool 90 such as tweezers can be inserted into the opening chamber 66 from the opening 65 to pull out the needle member 16 that is left on the needle guide jig 53.

Needless to say, in carrying out the present invention, as well as the specific form of the syringe unit, the specific forms of the frame body, the syringe guide jig, the needle guide jig, and the like, which constitute the needle attachment and detachment assist device may be modified variously. For example, several types of syringe guide jigs each having a guide hole of a size corresponding to that of a syringe to be applied may be prepared, and the syringe guide jig may be exchanged according to the type of a syringe. Alternatively, several types of needle guide jigs each having a needle insertion hole of a size corresponding to that of a needle member to be applied may be prepared, and the needle guide jig may be exchanged according to the type of a needle member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A needle attachment and detachment assist device for a syringe unit in which a syringe and a needle member are fixed to each other via a luer-lock-type joint, the needle attachment and detachment assist device comprising:
   a frame body;
   a syringe guide jig provided on an upper part of the frame body, and including a guide hole through which the syringe is inserted; and
   a needle guide jig provided on a lower part of the syringe guide jig to be opposed to the syringe guide jig, the needle guide jig including (i) a needle insertion hole, the needle insertion hole including a center hole portion located on a central axis of the guide hole, and (ii) a rib guide groove into which a rib extending in a direction along an axis of a body of the needle member is inserted, the rib guide groove being configured to prevent the needle member from rotating about the axis in a state in which the rib is inserted into the rib guide groove.

2. The needle attachment and detachment assist device of claim 1, wherein the frame body includes a pair of side plates, and a needle chamber which is defined by the needle guide jig and the pair of side plates under the needle guide jig.

3. The needle attachment and detachment assist device of claim 2, wherein the frame body includes a lower plate formed of an optically transparent material, and the lower plate is arranged at a position facing the needle chamber.

4. The needle attachment and detachment assist device of claim 1, wherein an opening chamber including an opening is provided between the syringe guide jig and the needle guide jig.

5. The needle attachment and detachment assist device of claim 1, wherein the guide hole of the syringe guide jig includes an inner surface formed such that an internal diameter of the guide hole is reduced downward in a tapered way in cross section.

6. The needle attachment and detachment assist device of claim 1, wherein a recess portion where a front end of a cylindrical proximal portion of the body contacts is provided around the center hole portion located at an upper surface of the needle guide jig.

* * * * *